United States Patent
Van Rijn et al.

(10) Patent No.: US 10,954,224 B2
(45) Date of Patent: Mar. 23, 2021

(54) DELTA-OPIOID RECEPTOR AGONISTS

(71) Applicant: Purdue Research Foundation, West Lafayette, IN (US)

(72) Inventors: Richard M Van Rijn, West Lafayette, IN (US); Mark S Cushman, West Lafayette, IN (US); Markus Lill, West Lafayette, IN (US); Robert J Cassell, West Lafayette, IN (US); Amr Hamed Mahmoud Abdallah, West Lafayette, IN (US); Mohamed S. A. Elsayed, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/620,907

(22) PCT Filed: Jun. 8, 2018

(86) PCT No.: PCT/US2018/036576
§ 371 (c)(1),
(2) Date: Dec. 10, 2019

(87) PCT Pub. No.: WO2018/231635
PCT Pub. Date: Dec. 20, 2018

(65) Prior Publication Data
US 2020/0199111 A1    Jun. 25, 2020

Related U.S. Application Data

(60) Provisional application No. 62/518,633, filed on Jun. 13, 2017.

(51) Int. Cl.
C07D 409/12 (2006.01)
A61P 25/32 (2006.01)
C07D 405/12 (2006.01)
C07D 417/12 (2006.01)

(52) U.S. Cl.
CPC ............ *C07D 409/12* (2013.01); *A61P 25/32* (2018.01); *C07D 405/12* (2013.01); *C07D 417/12* (2013.01)

(58) Field of Classification Search
CPC .. C07D 409/12; C07D 405/12; C07D 417/12; A61P 25/32
See application file for complete search history.

(56) References Cited

U.S. PATENT DOCUMENTS

| RE29,828 E | * | 11/1978 | Lunsford | C07D 207/14 548/557 |
| 2003/0176461 A1 | * | 9/2003 | Egle | C07D 401/06 514/317 |

FOREIGN PATENT DOCUMENTS

| WO | WO1994027967 A1 | * | 12/1994 | ........... C07D 211/58 |
| WO | WO-2014116684 A1 | * | 7/2014 | ........... C07D 401/14 |

OTHER PUBLICATIONS

Gendron; Pharmacological Reviews 2016, 68, 631-700; DOI: https://doi.org/10.1124/pr.114.008979 (Year: 2016).*
Van Rijn R. M., et al., β-Arrestin 2 dependence of δ opioid receptor agonists is correlated with alcohol intake. British Journal of Pharmacology (2016) 173 332-343.
Van Rijn R. M., et al., Distinctive modulation of ethanol place preference by delta opioid receptorselective agonists. Drug and Alcohol Dependence 122 (2012) 156-159.
Van Rijn R. M., et al., Dual Efficacy of Delta Opioid Receptor-Selective Ligands for Ethanol Drinking and Anxiety. TJPET 335:133-139, 2010.
Alongkronrusmee D., et al., Involvement of delta opioid receptors in alcohol withdrawal-induced mechanical allodynia in male C57BL/6 mice. Drug and Alcohol Dependence 167 (2016) 190-198.
Van Rijn R. M., et al., The δ1 Opioid Receptor Is a Heterodimer That Opposes the Actions of the δ2 Receptor on Alcohol Intake. Biol Psychiatry 2009;66:777-784.

* cited by examiner

*Primary Examiner* — Daniel R Carcanague
(74) *Attorney, Agent, or Firm* — Purdue Research Foundation; Zhigang Rao

(57) ABSTRACT

The present disclosure relates to novel δ-opioid receptor agonists, and the method of making and using the novel δ-opioid receptor agonists. The novel δ-opioid receptor agonists are selective δ-opioid receptor agonists that have substantially no beta-arrestin 2 recruitment or low beta-arrestin 2 recruitment. The novel δ-opioid receptor agonists may be used for the treatment for alcohol use disorders and other co-occurring psychiatric disorders.

3 Claims, No Drawings

DELTA-OPIOID RECEPTOR AGONISTS

CROSS-REFERENCE TO RELATED APPLICATIONS

This application is a national stage application of International Patent Application No. PCT/US18/36576, filed Jun. 8, 2018, which is related to and claims the benefits of U.S. Provisional Application Ser. No. 62/518,633, filed Jun. 13, 2017. The contents of which are incorporated herein entirely.

TECHNICAL FIELD

The present disclosure relates to novel δ-opioid (delta-opioid) receptor agonists, and the method of making and using the novel δ-opioid receptor agonists.

BACKGROUND

This section introduces aspects that may help facilitate a better understanding of the disclosure. Accordingly, these statements are to be read in this light and are not to be understood as admissions about what is or is not prior art.

Currently few Federal Drug Administration approved drugs may be used for the treatment of alcohol use disorders. Alcohol use disorder is a chronic relapsing condition that includes alcohol withdrawal syndrome and is also frequently co-morbid with chronic pain disorders and mood disorders such as depression and anxiety.

One approved drug for the treatment of alcohol use disorders is REVIA® (naltrexone hydrochloride). Naltrexone is a non-selective opioid receptor antagonist with moderate efficacy but suffers from adverse effects and does not treat associated depression, chronic pain or anxiety.

The four opioid receptor subtypes are mu, delta, kappa, and nociceptin receptors. Each receptor is able to interact with G-proteins that inhibit adenylyl cyclase and thus reduce intracellular cAMP levels. It is known that certain conformations of the receptor favor interaction with the beta-arrestin family of proteins. Interaction with these beta-arrestins may lead to activation of different (non-cAMP) signal transduction pathways and can modulate unique types of physiological responses, some of which may result in adverse effects.

So far, there is no FDA approved δ-opioid receptor agonist for the treatment for alcohol use disorders, depression or anxiety.

Therefore, there is a need for novel agents for the treatment for alcohol use disorders and other co-occurring psychiatric disorders.

SUMMARY

The present invention provides novel δ-opioid receptor agonists that induce no or undetectable recruitment of beta-arrestin 2. The novel δ-opioid receptor agonists in the present disclosure may provide potential novel treatments for alcohol use disorder and other co-occurring psychiatric disorders.

Specifically, the compounds of the present invention are represented in Formula I:

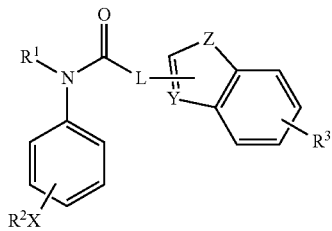

or a pharmaceutically acceptable salt or hydrate thereof, wherein:

$R^1$ is a 3-8 membered nitrogen-containing saturated heterocyclic ring, wherein the hydrogen on the nitrogen is optionally substituted with a C1-C8 alkyl, a C1-C8 alkenyl, a C3-C8 cycloalkyl, or a C3-C8 cycloalkenyl, wherein said C1-C8 alkyl, C1-C8 alkenyl, C3-C8 cycloalkyl, or C3-C8 cycloalkenyl is optionally substituted with one or more substituents selected from the group consisting of halogen, hydroxyl, C1-C8 alkoxy, phenyl, thiophenyl, furyl, pyridyl, naphthyl and any combination thereof;

$R^2X$ represents 1-4 same or different substituents with X directly attached to aromatic ring, wherein $R^2$ in each of said 1-4 substituents is independently selected from the group consisting of H, C1-C8 alkyl, C1-C8 alkenyl, C3-C8 cycloalkyl, and C3-C8 cycloalkenyl, wherein said C1-C8 alkyl, C1-C8 alkenyl, C3-C8 cycloalkyl, and C3-C8 cycloalkenyl is optionally substituted with one or more substituents selected from the group consisting of halogen, hydroxyl, C1-C8 alkoxy, and any combination thereof;

$R^3$ represents 1-4 substituents, each of said 1-4 substituents is independently selected from the group consisting of hydrogen, halogen, C1-C8 alkyl, C1-C6 alkoxy;

L is N, O, or a bond;

X is N, O or S;

Y is $CR^4$ or N, wherein $R^4$ is H, C1-C8 alkyl, or halogen; and

Z is $CR^5R^6$, $NR^7$, O or S, wherein $R^5$-$R^7$ are each independently H, C1-C8 alkyl, or halogen.

In one embodiment, the present disclosure provides methods of using a composition comprising a compound of Formula I for the treatment for alcohol use disorders and other co-occurring psychiatric disorders.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

Non-limiting examples of substituents, that can be bonded to a substituted carbon (or other such as nitrogen) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, (CH$_2$)$_{0-2}$P(O)OR$_2$, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)C(O)OR, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R wherein R can be hydrogen or a carbon-based moiety, and wherein the carbon-based moiety can itself be further substituted; for example, wherein R can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R can be independently mono- or multi-substituted; or wherein two R groups bonded to a nitrogen atom or to adjacent nitrogen atoms can together with the nitrogen atom or atoms form a heterocyclyl, which can be mono- or independently multi-substituted.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidinyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The terms "halo," "halogen," or "halide" group, as used herein, by themselves or as part of another substituent, mean, unless otherwise stated, a fluorine, chlorine, bromine, or iodine atom. The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

The term "optionally substituted," or "optional substituents," as used herein, means that the groups in question are either unsubstituted or substituted with one or more of the substituents specified. When the groups in question are substituted with more than one substituent, the substituents may be the same or different. When using the terms "independently," "independently are," and "independently selected from" mean that the groups in question may be the same or different. Certain of the herein defined terms may occur more than once in the structure, and upon such occurrence each term shall be defined independently of the other.

As used herein, the term "salts" and/or "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The present invention provides novel δ-opioid receptor agonists as potential treatments for alcohol use disorder and other co-occurring psychiatric disorders. Accordingly, the present invention provides a compound of Formula I:

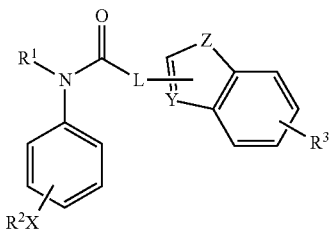

or a pharmaceutically acceptable salt or hydrate thereof, wherein:
- $R^1$ is a 3-8 membered nitrogen-containing saturated heterocyclic ring, wherein the hydrogen on the nitrogen is optionally substituted with a C1-C8 alkyl, a C1-C8 alkenyl, a C3-C8 cycloalkyl, or a C3-C8 cycloalkenyl, wherein said C1-C8 alkyl, C1-C8 alkenyl, C3-C8 cycloalkyl, or C3-C8 cycloalkenyl is optionally substituted with one or more substituents selected from the group consisting of halogen, hydroxyl, C1-C8 alkoxy, phenyl, thiophenyl, furyl, pyridyl, naphthyl, and any combination thereof;
- $R^2X$ represents 1-4 same or different substituents with X directly attached to aromatic ring, wherein $R^2$ in each of said 1-4 substituents is independently selected from the group consisting of H, C1-C8 alkyl, C1-C8 alkenyl, C3-C8 cycloalkyl, and C3-C8 cycloalkenyl, wherein said C1-C8 alkyl, C1-C8 alkenyl, C3-C8 cycloalkyl, and C3-C8 cycloalkenyl is optionally substituted with one or more substituents selected from the group consisting of halogen, hydroxyl, C1-C8 alkoxy, and any combination thereof;
- $R^3$ represents 1-4 substituents, each of said 1-4 substituents is independently selected from the group consisting of hydrogen, halogen, C1-C8 alkyl, C1-C6 alkoxy;
- L is N, O, or a bond;
- X is N, O or S;
- Y is $CR^4$ or N, wherein $R^4$ is H, C1-C8 alkyl, or halogen; and
- Z is $CR^5R^6$, $NR^7$, O or S, wherein $R^5$-$R^7$ are each independently H, C1-C8 alkyl, or halogen.

In one embodiment, the present invention provides a compound of Formula I or a pharmaceutically acceptable salt or hydrate thereof, wherein the preferred $R^1$ is a piperidinyl or a pyrrolidinyl, wherein the hydrogen on the nitrogen of the piperidinyl or pyrrolidinyl ring is optionally substituted with a C1-C4 alkyl, a C1-C4 alkenyl, a C3-C8 cycloalkyl, or a C3-C8 cycloalkenyl, wherein said C1-C4 alkyl, C1-C4 alkenyl, C3-C8 cycloalkyl, or C3-C8 cycloalkenyl is optionally substituted with one or more substituents selected from the group consisting of halogen, hydroxyl, C1-C4 alkoxy, phenyl, thiophenyl, furyl, pyridyl, and naphthyl, and any combination thereof.

In one embodiment, the present invention provides a compound of Formula I or a pharmaceutically acceptable salt or hydrate thereof, wherein the preferred $R^2X$ represents 1-2 substituents with X directly attached to the phenyl ring, wherein $R^2$ in each of said 1-2 substituents is independently selected from the group consisting of H, C1-C4 alkyl, C1-C4 alkenyl, C3-C8 cycloalkyl, and C3-C8 cycloalkenyl, wherein said C1-C4 alkyl, C1-C4 alkenyl, C3-C8 cycloalkyl, and C3-C8 cycloalkenyl is optionally substituted with one or more substituents selected from the group consisting of halogen, hydroxyl, C1-C4 alkoxy, and any combination thereof, and wherein X is O.

In one embodiment, the present invention provides a compound of Formula I or a pharmaceutically acceptable salt or hydrate thereof, wherein the preferred $R^3$ represents 1-2 substituents, each of said 1-2 substituents is independently selected from the group consisting of halogen, C1-C4 alkyl, and C1-C4 alkoxy.

In one embodiment, the present invention provides a compound of Formula I or a pharmaceutically acceptable salt or hydrate thereof, wherein the preferred L is a bond.

In one embodiment, the present invention provides a compound of Formula I or a pharmaceutically acceptable salt or hydrate thereof, wherein the preferred X is O.

In one embodiment, the present invention provides a compound of Formula I or a pharmaceutically acceptable salt or hydrate thereof, wherein the preferred Z is NH, O or S.

In one embodiment, the present invention provides a compound of Formula I or a pharmaceutically acceptable salt or hydrate thereof, wherein the preferred Y is $CR^4$, wherein $R^4$ is H, C1-C4 alkyl, or halogen.

In one embodiment, the present invention provides a compound of Formula I, or a pharmaceutically acceptable salt or hydrate thereof, wherein:
- $R^1$ is a piperidinyl or a pyrrolidinyl, wherein the hydrogen on the nitrogen of the piperidinyl or pyrrolidinyl ring is optionally substituted with a C1-C4 alkyl, a C1-C4 alkenyl, a C3-C8 cycloalkyl, or a C3-C8 cycloalkenyl, wherein said C1-C4 alkyl, C1-C4 alkenyl, C3-C8 cycloalkyl, or C3-C8 cycloalkenyl is optionally substituted with one or more substituents selected from the group consisting of halogen, hydroxyl, C1-C4 alkoxy, phenyl, thiophenyl, furyl, pyridyl, and naphthyl, and any combination thereof;
- $R^2X$ represents 1-2 substituents with X directly attached to the phenyl ring, wherein $R^2$ in each of said 1-2 substituents is independently selected from the group consisting of H, C1-C4 alkyl, C1-C4 alkenyl, C3-C8 cycloalkyl, and C3-C8 cycloalkenyl, wherein said C1-C4 alkyl, C1-C4 alkenyl, C3-C8 cycloalkyl, and C3-C8 cycloalkenyl is optionally substituted with one or more substituents selected from the group consisting of halogen, hydroxyl, C1-C4 alkoxy, and any combination thereof, and wherein X is O;
- $R^3$ represents 1-2 substituents, each of said 1-2 substituents is independently selected from the group consisting of halogen, C1-C4 alkyl, and C1-C4 alkoxy;
- L is a bond;
- X is O;
- Y is $CR^4$, wherein $R^4$ is H, C1-C4 alkyl, or halogen; and
- Z is NH, O or S.

In one embodiment, the present invention provides a compound of Formula I, or a pharmaceutically acceptable salt or hydrate thereof, wherein:
- $R^1$ is a piperidinyl or a pyrrolidinyl, wherein the hydrogen on the nitrogen of the piperidinyl or pyrrolidinyl ring is substituted with a C1-C4 alkyl, wherein said C1-C4 alkyl is optionally substituted with a phenyl;
- $R^2X$ represents 1-2 substituents with X directly attached to phenyl ring, wherein $R^2$ in each of said 1-2 substituents is independently selected from the group consisting of H, C1-C4 alkyl;
- $R^3$ represents 1-2 substituents, each of said 1-2 substituents is independently selected from the group consisting of F, Cl, Br, and C1-C4 alkyl;
- L is a bond;
- X is O;
- Y is $CR^4$, wherein $R^4$ is H, C1-C4 alkyl, or halogen; and
- Z is NH, O or S.

In one embodiment, the present invention provides a composition comprising a compound of Formula I, or a pharmaceutically acceptable salt or hydrate thereof, in any embodiment of the present disclosure.

In one embodiment, the present invention provides a compound selected from the group consisting of:

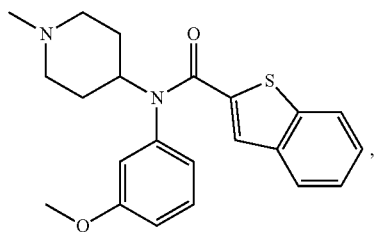

,

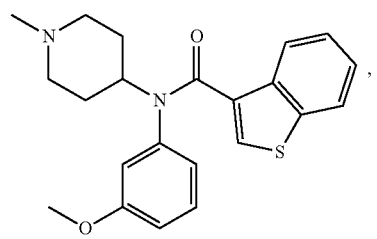

,

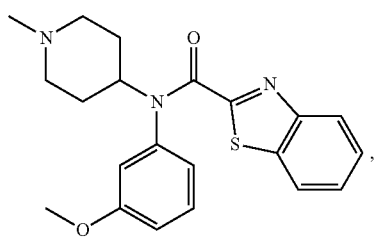

,

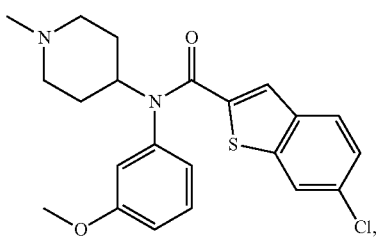

,

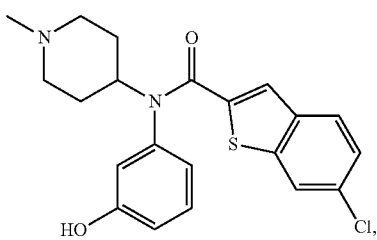

,

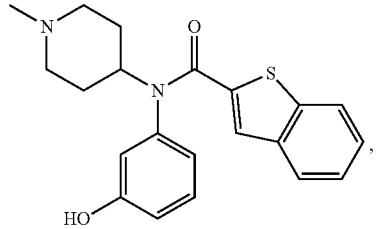

,

-continued

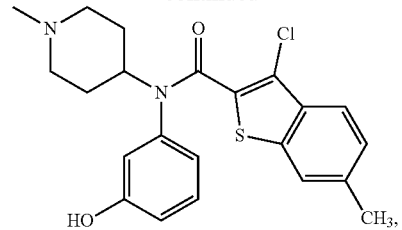

,

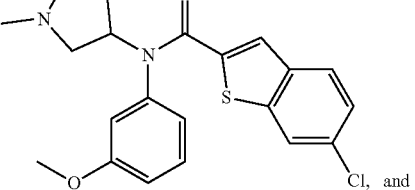

, and

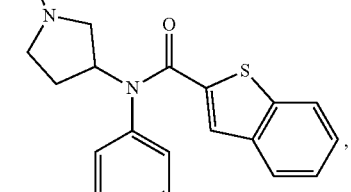

,

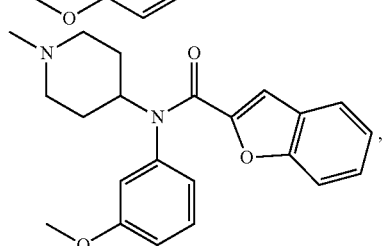

,

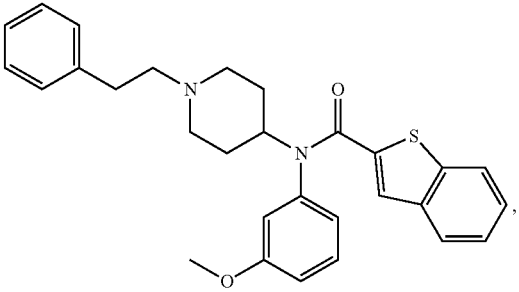 [SMILES: COc1cccc(N(C(=O)c2cc3ccccc3s2)C2CCN(CCc3ccccc3)CC2)c1]

and a pharmaceutically acceptable salt or hydrate thereof.

In one embodiment, the present invention provides a compound of Formula I or a pharmaceutically acceptable salt or hydrate thereof in any embodiment as a δ-opioid receptor agonist.

In one embodiment, the present invention provides a compound of Formula I or a pharmaceutically acceptable salt or hydrate thereof in any embodiment as a δ-opioid receptor agonist with substantially no beta-arrestin 2 recruitment or low beta-arrestin 2 recruitment.

In one embodiment, the present invention provides a compound of Formula I in any embodiment for the treatment for alcohol use disorders.

In one embodiment, the present invention provides a compound of Formula I in any embodiment for the treatment for psychiatric disorders.

In one embodiment, the present invention provides a compound of Formula I for the treatment for alcohol use disorders and other co-occurring psychiatric disorders.

The present invention further provides a method of treating alcohol use disorders in a patient, comprising administering to a patient in need thereof an effective amount of a compound of Formula I, or a pharmaceutically acceptable salt thereof. The present invention also provides a method of agonizing the δ-opioid receptor in a patient, comprising administering to a patient in need thereof an effective amount of a compound of Formula I, or a pharmaceutically acceptable salt thereof.

Furthermore, this disclosure provides a compound of Formula I, or a pharmaceutically acceptable salt thereof for use in therapy, in particular for the treatment of alcohol use disorders. In addition, this invention provides a compound of Formula I, or a pharmaceutically acceptable salt thereof for use in preventing alcohol use disorders. Even furthermore, this invention provides the use of a compound of Formula I, or a pharmaceutically acceptable salt thereof, for the manufacture of a medicament for the treatment of alcohol use disorders or for preventing alcohol use disorders.

The present disclosure further provides a pharmaceutical composition, comprising a compound of Formula I, or a pharmaceutically acceptable salt thereof, with one or more pharmaceutically acceptable carriers, diluents, or excipients. The present disclosure further provides a process for preparing a pharmaceutical composition, comprising admixing a compound of Formula I, or a pharmaceutically acceptable salt thereof, with one or more pharmaceutically acceptable carriers, diluents, or excipients. This present disclosure also encompasses novel intermediates and processes for the synthesis of the compounds of Formula I.

The compounds of the present invention may be prepared by a variety of procedures, some of which are illustrated in Scheme 1 below. Some substituents may be eliminated in the following schemes for the sake of clarity and are not intended to limit the teaching of the schemes in any way. Certain protection and/or de-protection step may be needed based on certain specific substitution pattern of certain compounds.

In general, any Example disclosed in the present disclosure may be prepared by the synthetic method as illustrated in Scheme 1, which is the method of preparing Example 1. One suitably substituted aniline compound such as 3-methoxyaniline may be treated with a suitably substituted heterocyclic ketone compound such as 1-methylpiperidin-4-one, under reductive amination conditions well-known to skilled artisan to afford an intermediate such as N-(3-methoxyphenyl)-1-methylpiperidin-4-amine, which may be further reacted with an acylation agent such as benzo[b]thiophene-2-carbonyl chloride to provide the desired final Example such as Example 1.

Example 1

N-(3-methoxyphenyl)-N-(1-methylpiperidin-4-yl)benzo[b]thiophene-2-carboxamide

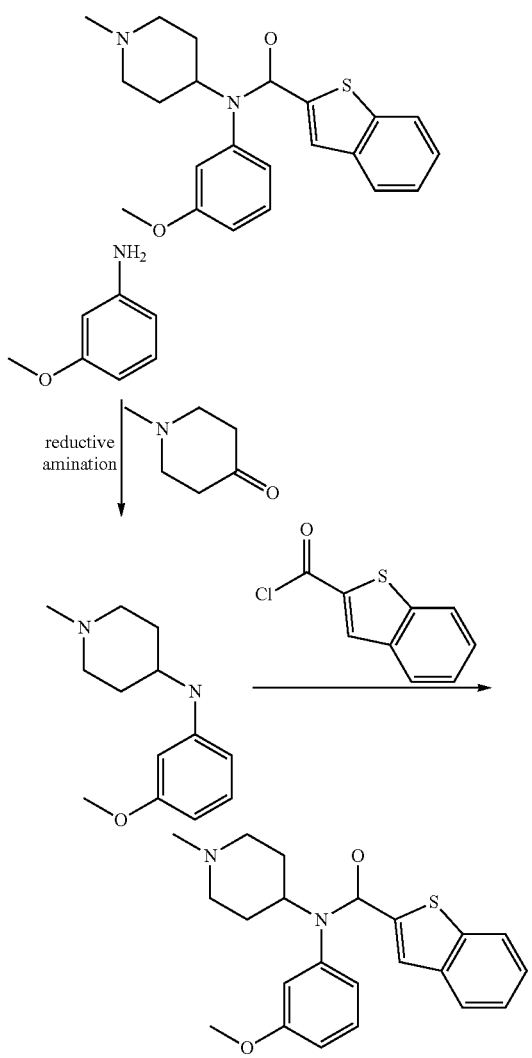

Scheme 1 Synthetic method of Example 1

N-(3-Methoxyphenyl)-1-methylpiperidin-4-amine: To a dry 50 mL round bottomed flask cooled in an iced bath was added 0.5 g (4.1 mmol, 1 eq.) 3-methoxyaniline and 0.46 g (4.1 mmol, 1 eq) 1-methylpiperidin-4-one. The reactants were solvated by addition of a mixture of 1,2-dichloroethane (8 mL) and ethanoic acid (1.5 mL) and stirred on ice for one hour. Maintaining the ice bath, 1.3 g (6.5 mmol, 1.6 eq) of sodium triacetoxyborohydride was slowly added. Following addition, the reaction mixture was allowed to return to room temperature and stirred for 20 hours. The resulting reaction mixture was diluted with 15 mL ethyl acetate, basified with 10 mL 5M sodium hydroxide and the organic fraction separated. The aqueous fraction was extracted with 2×10 mL of ethyl acetate and the organic fractions combined and washed with 2×15 mL water followed by 15 mL brine, dried over sodium sulfate and the solvent removed on a rotary evaporator. The resultant brown oil was purified by column chromatography over silica gel utilizing a chloroform/methanol/triethylamine mobile phase (initial ratio 97:3:0 increasing to 90:5:5 CHCl$_3$:MeOH:TEA once product detected by TLC) to yield after evaporation 0.80 g of N-(3-methoxyphenyl)-1-methylpiperidin-4-amine (3.6 mmol, 88% yield).

benzo[b]thiophene-2-carbonyl chloride: To a dry 25 mL round bottomed flask was added 44 mg (0.25 mmol) benzo[b]thiophene-2-carboxylic acid and excess (5 mL) thionyl chloride, and the resulting mixture held at reflux for 3 h. The resulting benzo[b]thiophene-2-carbonyl chloride was then evaporated to dryness via rotavap in preparation for the next step.

N-(3-methoxyphenyl)-N-(1-methylpiperidin-4-yl)benzo[b]thiophene-2-carboxamide: To a dry 25 mL round bottomed flask was added 50 mg (0.23 mmol, 1 eq.) N-(3-methoxyphenyl)-1-methylpiperidin-4-amine and 115 mg triethylamine (1.1 mmol, 5 eq.) and the resulting mixture solubilized with 5 mL dry dichloromethane. The mixture was then cooled on an ice bath and the previously prepared benzo[b]thiophene-2-carbonyl chloride (49 mg, 0.25 mmol, 1.1 eq.) was solubilized in 2 mL dry dichloromethane and added slowly to the reaction mixture with stirring. Following addition, the mixture was held at reflux for 20 h and then quenched with 20 mL saturated sodium bicarbonate and the organic fraction separated. The aqueous fraction was extracted with 2×10 mL chloroform and the combined organic fractions washed with 2×15 mL water, 15 mL brine, dried over sodium sulfate and the solvent removed by rotavap. The resultant brown solid was then re-dissolved in a minimum of chloroform and purified by column chromatography over silica gel utilizing a chloroform/methanol/triethylamine mobile phase (initial ratio 96:4:0 increasing to 92:4:4 CHCl$_3$:MeOH:TEA once product detected by TLC) to yield after evaporation 46 mg N-(3-methoxyphenyl)-N-(1-methylpiperidin-4-yl)benzo[b]thiophene-2-carboxamide (0.12 mmol, 52% yield). MALDI m/z [M+H]$^+$ 381, HR-LC/MS m/z [M+H]$^+$ calcd 381.1632, actual 381.1631.

TABLE 1

Examples 2-9 are prepared with essentially the same or similar method of preparing Example 1.

| Examples | Structures | Chemical names |
|---|---|---|
| 2 | 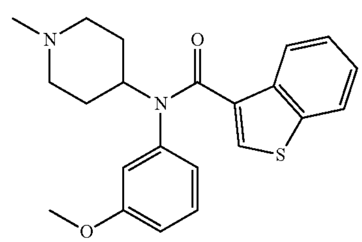 [SMILES: COc1cccc(N(C(=O)c2csc3ccccc23)C2CCN(C)CC2)c1] | N-(3-methoxyphenyl)-N-(1-methylpiperidin-4-yl)benzo[b]thiophene-3-carboxamide |
| 3 | 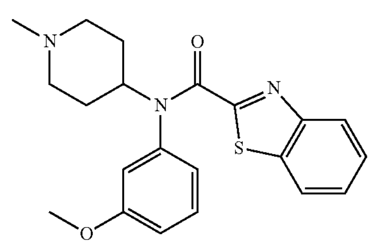 [SMILES: COc1cccc(N(C(=O)c2nc3ccccc3s2)C2CCN(C)CC2)c1] | N-(3-methoxyphenyl)-N-(1-methylpiperidin-4-yl)benzo[d]thiazole-2-carboxamide |
| 4 | 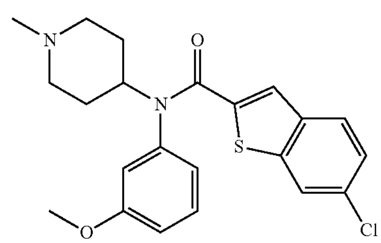 [SMILES: COc1cccc(N(C(=O)c2cc3ccc(Cl)cc3s2)C2CCN(C)CC2)c1] | 6-chloro-N-(3-methoxyphenyl)-N-(1-methylpiperidin-4-yl)benzo[b]thiophene-2-carboxamide |
| 5 | 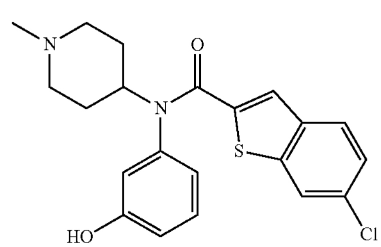 [SMILES: CN1CCC(N(C(=O)c2cc3ccc(Cl)cc3s2)c2cccc(O)c2)CC1] | 6-chloro-N-(3-hydroxyphenyl)-N-(1-methylpiperidin-4-yl)benzo[b]thiophene-2-carboxamide |

TABLE 1-continued

Examples 2-9 are prepared with essentially the same or similar method of preparing Example 1.

| Examples | Structures | Chemical names |
|---|---|---|
| 6 | 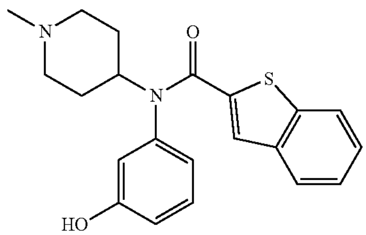 [SMILES: CN1CCC(N(C(=O)c2cc3ccccc3s2)c2cccc(O)c2)CC1] | N-(3-hydroxyphenyl)-N-(1-methylpiperidin-4-yl)benzo[b]thiophene-2-carboxamide |
| 7 | 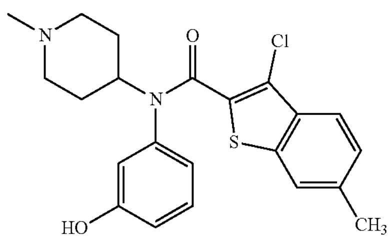 | 3-chloro-N-(3-hydroxyphenyl)-6-methyl-N-(1-methylpiperidin-4-yl)benzo[b]thiophene-2-carboxamide |
| 8 | 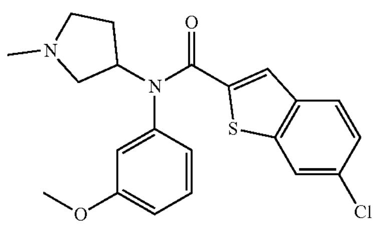 [SMILES: COc1cccc(N(C(=O)c2cc3ccc(Cl)cc3s2)C2CCN(C)C2)c1] | 6-chloro-N-(3-methoxyphenyl)-N-(1-methylpyrrolidin-3-yl)benzo[b]thiophene-2-carboxamide |
| 9 | 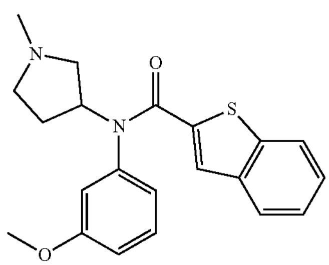 [SMILES: COc1cccc(N(C(=O)c2cc3ccccc3s2)C2CCN(C)C2)c1] | N-(3-methoxyphenyl)-N-(1-methylpyrrolidin-3-yl)benzo[b]thiophene-2-carboxamide |
| 10 | 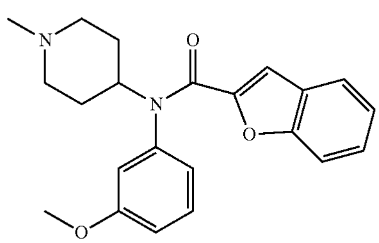 [SMILES: COc1cccc(N(C(=O)c2cc3ccccc3o2)C2CCN(C)CC2)c1] | N-(3-methoxyphenyl)-N-(1-methylpiperidin-4-yl)benzofuran-2-carboxamide |
| 11 | 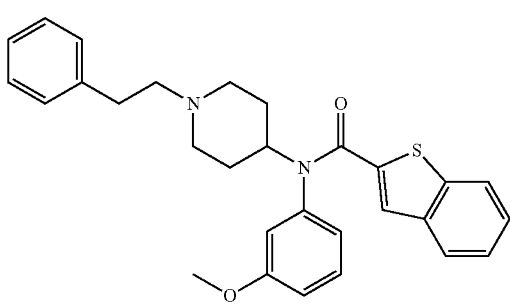 [SMILES: COc1cccc(N(C(=O)c2cc3ccccc3s2)C2CCN(CCc3ccccc3)CC2)c1] | N-(3-methoxyphenyl)-N-(1-phenethylpiperidin-4-yl)benzo[b]thiophene-2-carboxamide |

TABLE 2

NMR data for Examples 2-9 and MS data for Examples 10-11:

| Examples | $^1$H NMR (500 MHz, CDCl$_3$) δ/Mass |
|---|---|
| 2 | 8.18 (d, J = 8.1 Hz, 1 H), 7.79 (d, J = 8.0 Hz, 1 H), 7.47 (dd, J = 11.1, 4.0 Hz, 1 H), 7.39 (s, 1 H), 7.13 (t, J = 8.1 Hz, 1 H), 7.06 (s, 1 H), 6.80-6.74 (m, 1 H), 6.68 (d, J = 7.7 Hz, 1 H), 6.64 (t, J = 2.2 Hz, 1 H), 4.93 (s, 1 H), 3.68 (s, 3 H), 3.11 (m, 2 H), 2.42 (m, 5 H), 2.06 (d, J = 14.2 Hz, 2 H), 1.85 (m, 2 H) |
| 3 | 8.12 (d, J = 8.7 Hz, 1 H), 7.98 (d, J = 8.1 Hz, 1 H), 7.90 (d, J = 8.8 Hz, 1 H), 7.68 (d, J = 8.6 Hz, 1 H), 7.61 (d, J = 9.1 Hz, 1 H), 7.59-7.55 (m, 1 H), 7.50 (d, J = 8.1 Hz, 1 H), 6.36 (s, 1 H), 6.18 (d, J = 14.9 Hz, 1 H), 3.85 (s, 3 H), 3.54 (d, J = 7.0 Hz, 1 H), 3.35 (m, 1 H), 2.70 (s, 3 H), 2.28 (m, 2 H), 2.03 (m, 3 H) |
| 4 | 7.67 (d, J = 1.2 Hz, 1 H), 7.48 (t, J = 8.3 Hz, 1 H), 7.31 (t, J = 8.1 Hz, 1 H), 7.22 (dd, J = 8.6, 1.8 Hz, 1 H), 6.99 (dd, J = 8.4, 2.5 Hz, 1 H), 6.88 (s, 1 H), 6.84-6.78 (m, 1 H), 6.74 (t, J = 2.2 Hz, 1 H), 4.77 (ddd, J = 15.9, 7.9, 3.9 Hz, 1 H), 3.80 (s, 3 H), 2.89 (d, J = 11.1 Hz, 2 H), 2.25 (s, 3 H), 2.14 (t, J = 11.4 Hz, 2 H), 1.89 (m, 2 H), 1.60 (m, 2 H) |
| 5 | 7.66 (s, 1 H), 7.48 (t, J = 7.1 Hz, 1 H), 7.20 (dd, J = 8.6, 1.9 Hz, 1 H), 7.15 (t, J = 8.0 Hz, 1 H), 6.86 (s, 1 H), 6.61 (dd, J = 15.4, 8.0 Hz, 2 H), 6.47 (s, 1 H), 4.88 (t, J = 12.1 Hz, 1 H), 3.01 (s, 2 H), 2.35 (s, 3 H), 1.95 (s, 1 H), 1.85-1.57 (m, 5 H), 1.25 (m, 3 H), 1.00 (t, J = 7.3 Hz, 1 H), 0.90 (s, 3 H) |
| 6 | 7.67 (d, J = 8.0 Hz, 1 H), 7.57 (d, J = 7.9 Hz, 1 H), 7.31-7.26 (m, 1 H), 7.22 (d, J = 7.0 Hz, 1 H), 7.14 (t, J = 8.0 Hz, 1 H), 6.91 (s, 1 H), 6.65-6.56 (m, 2 H), 6.48 (d, J = 2.0 Hz, 1 H), 4.89 (t, J = 12.2 Hz, 1 H), 3.02 (m, 2 H), 2.35 (m, 4 H), 2.00-1.58 (m, 5 H), 1.24 (m, 1 H) |
| 7 | 7.58 (d, J = 8.2 Hz, 1 H), 7.39 (s, 1 H), 7.17 (d, J = 8.2 Hz, 1 H), 6.92 (t, J = 7.7 Hz, 1 H), 6.52 (d, J = 7.8 Hz, 1 H), 6.45 (s, 1 H), 6.36 (d, J = 8.2 Hz, 1 H), 4.84 (m, 1 H), 3.04 (m, 2 H), 2.40 (s, 3 H), 2.33 (m, 4 H), 1.73 (m, 5 H) |
| 8 | 7.67 (d, J = 1.8 Hz, 1 H), 7.50 (d, J = 8.6 Hz, 1 H), 7.34 (t, J = 8.1 Hz, 1 H), 7.22 (dd, J = 8.6, 1.9 Hz, 1 H), 7.00 (dd, J = 8.0, 2.1 Hz, 1 H), 6.88 (d, J = 3.6 Hz, 1 H), 6.86 (d, J = 7.9 Hz, 1 H), 6.81 (s, 1 H), 5.14 (m, 1 H), 3.81 (s, 3 H), 3.02 (m, 1 H), 2.65 (m, 2 H), 2.54 (m, 1 H), 2.34 (s, 3 H), 2.27 (m, 1 H), 1.93 (m, 1 H), 1.64 (m, 1 H) |
| 9 | 7.70 (d, J = 8.0 Hz, 1 H), 7.59 (d, J = 7.6 Hz, 1 H), 7.33 (dd, J = 11.3, 4.7 Hz, 1 H), 7.30 (dd, J = 8.1, 1.2 Hz, 1 H), 7.28-7.27 (m, 1 H), 7.02-6.97 (m, 1 H), 6.93 (s, 1 H), 6.87 (d, J = 7.8 Hz, 1 H), 6.82 (d, J = 2.0 Hz, 1 H), 5.20-5.11 (m, 1 H), 3.81 (s, 3 H), 3.04 (s, 1 H), 2.66 (m, 2 H), 2.55 (m, 1 H), 2.35 (s, 3 H), 2.26 (m, 1 H), 1.94 (m, 1 H) |
| 10 | 365.2 (M + 1) |
| 11 | 471.2 (M + 1) |

Biological Evaluation

The biological evaluation methods can be found in T Chiang, K Sansuk and R M van Rijn, β-Arrestin 2 dependence of δ opioid receptor agonists is correlated with alcohol intake, British Journal of Pharmacology (2016) 173 332-343

Fluorescent Binding assay: Performed using the Tag-lite assay according to the manufacturer's protocol (Cis-Bio, Bedford, Mass., USA). Tb-labeled HEK293-SNAP-hDOR cells/well (4000 cells/well) were plated in 10 µl Tag-lite medium into low-volume 384 well plates in the presence of 5 µl 8 nM fluorescent naltrexone (final concentration) and 5 µl of an increasing concentration of unlabeled δ receptor agonists and incubated at room temperature for 3 hours and homogenous time-resolved fluorescence was measured on a Flexstation3 (Molecular Devices, Sunnyvale, Calif., USA). Data were plotted using GRAPHPAD PRISM 5 software (GraphPad Software, La Jolla, Calif., USA). Example 1 is a δ-opioid receptor agonist with a $pK_i$ value of 5.10 (n=2, SEM=0.05)

Radioligand binding assay: CHO-OPRD or OPRM PathHunter β-arrestin 2 cells (DiscoverX, Fremont, Calif., USA) membranes were prepared by ultrasonic disruption of the cell followed by ultracentrifugation. 100 µl of the membranes (5-10 µg protein) was incubated with 50 µl of an increasing concentration of unlabeled δ receptor agonists and 50 µl of a fixed concentration of [$^3$H]DPDPE or [$^3$H]DAMGO (Perkin Elmer, Waltham, Mass., USA. final concentration 0.5-5 nM), for assessing affinity respectively at DOR or MOR, and incubated for 90 minutes, before filtration through a GF-B filter (Perkin Elmer). Radioligand binding was assessed using a scintillation Topcount (Packard Bioscience/Perkin Elmer). Data were plotted using GRAPHPAD PRISM 5 software (GraphPad Software, La Jolla, Calif., USA). Example 1 is a δ-opioid receptor agonist with a $pK_i$ value of 5.14 (n=2, SEM=0.06) and lower value for the opioid receptor with a $pK_i$ value of 4.93 (n=2, SEM=0.02)

cAMP inhibition assay: HEK 293FT (Life Technologies, Grand Island, N.Y., USA) cells were transfected with pcDNA3.1-FLAGDOR or HAMOR and pGloSensor22F-cAMP plasmids (Promega, Madison, Wis., USA) in a 3:7 ratio using X-tremeGENE9 (Roche, Indianapolis, Ind., USA) according to manufacturer's protocol. On day 2, cells were dislodged and counted, and 7.5 µL of cell suspension was seeded (25 000 cells/well) in a low volume, round bottom white 384-well CulturPlate-384 (Perkin Elmer, Waltham, Mass., USA). Four hours later, cells were stimulated with 7.5 µL 4% GloSensor reagent (Promega) in HBSS/HEPES (Life Technologies) and incubated for 90 min at room temperature. Cells were stimulated for 20 min with a dilution series of δ receptor agonists (5 µL per well). Each dilution was performed in triplicate. Following stimulation, cells were incubated for 15 min with 5 µL 31.6 µM forskolin (Sigma, St. Louis, Mo., USA), and luminescence was measured on a Flexstation3 (Molecular Devices, Sunnyvale, Calif., USA). Data were plotted using GRAPHPAD PRISM 5 software (GraphPad Software, La Jolla, Calif., USA). Potency of δ-opioid receptor agonists to inhibit cAMP production is depicted as concentration of 50% inhibition ($pIC_{50}$) and the SEM. Example 1 is a potent δ-opioid receptor agonist with a $pIC_{50}$ value of 6.37 (n=3, SEM=0.06), but a weak partial agonist at the µ-opioid receptor.

β-Arrestin 2 recruitment assay: CHO-OPRD PathHunter β-arrestin 2 cells (DiscoverX, Fremont, Calif., USA) were seeded (2500 cells per well) in a low volume, round bottom 384-well plate. The next day, cells were stimulated for 90 min with a dilution series of δ receptor agonists at 37° C./5% $CO_2$. Each dilution was performed in triplicate. β-Arrestin 2 recruitment was detected following a 60 min incubation period with PathHunter reagent according to the manufacturer's guidelines. Luminescence was measured using a Flexstation3. Data were plotted using GRAPHPAD PRISM 5 software. Potency of δ-opioid receptor agonists in recruiting β-arrestin 2 at the δ-opioid receptor expressed in CHO cells is depicted with $pEC_{50}$. Example 1 demonstrates zero β-arrestin 2 efficacy.

Voluntary alcohol intake assay: C57BL/6 wild-type adult male mice were exposed to a limited access (4 hours/day), 2-bottle choice (water vs. 10% ethanol), drinking-in-the-dark (DID) protocol during their active cycle (dark phase) until the alcohol intake was stable. Bottle weights were measured directly before and after the 4-hour access period to the second decimal point to determine fluid intake during this access period. Weights of bottles were corrected for any spillage with fluid bottles placed on empty cages. After three weeks of exposure to the drinking model described above, alcohol and water intake on the day of infusion (Friday) was compared with the average alcohol intake over the preceding three days (Tuesday-Thursday) to determine if drug injection altered voluntary alcohol intake. Mice were injected with i.p. saline for vehicle measurements in week 4 and the following weeks with increasing doses of i.p. injected Example 1; 3 mg/kg in week 5 and 10 mg/kg in week 6. Example 1 dose-dependently decreased alcohol use in wild-type C57BL/6 adult male mice. Group size was 10 animals. Data were plotted using GRAPHPAD PRISM 5 software.

Voluntary alcohol intake assay: C57BL/6 δ-opioid receptor knockout adult male mice were exposed to a limited access (4 hours/day), 2-bottle choice (water vs. 10% ethanol), drinking-in-the-dark (DID) protocol during their active cycle (dark phase) until the alcohol intake was stable. Bottle weights were measured directly before and after the 4-hour access period to the second decimal point to determine fluid intake during this access period. Weights of bottles were corrected for any spillage with fluid bottles placed on empty cages. After three weeks of exposure to the drinking model described above, alcohol and water intake on the day of infusion (Friday) was compared with the average alcohol intake over the preceding three days (Tuesday-Thursday) to determine if drug injection altered voluntary alcohol intake. Mice were injected with i.p. saline for vehicle measurements in week 4 and the following weeks with increasing doses of i.p. injected Example 1; 3 mg/kg in week 5 and 10 mg/kg in week 6. Group size was 10 animals. Data were plotted using GRAPHPAD PRISM 5 software. Example 1 did not decreased alcohol use in δ-opioid receptor knockout C57BL/6 adult male mice. This indicates the physiological effect of Example 1 to attenuate alcohol use depends on the presence of δ-opioid receptors.

Square locomotor boxes from Med Associates (L 27.3 cm×W 27.3 cm×H 20.3 cm, St. Albans Vt., USA) were used to monitor locomotor activity during the active/dark phase of wild-type C57BL/6 adult male mice. Animals were habituated to the locomotor boxes for 60 minutes one day prior to drug testing. On test day animals were injected i.p. with saline or 3 mg/kg of Example 1 and locomotor activity was tracked for 90 minutes. Mice injected with Example 1 did not differ in their locomotor activity compared to saline injected mice. Group size was 5-6 animals. Data were plotted using GRAPHPAD PRISM 5 software.

Therefore, Example 1 is a δ-opioid receptor agonist with substantially no beta-arrestin 2 recruitment or low beta-arrestin 2 recruitment, and may be used for the treatment for alcohol use disorders and other co-occurring psychiatric disorders.

Any compound of Formula I as disclosed in the present disclosure that is a δ-opioid receptor agonist with substantially no beta-arrestin 2 recruitment or low beta-arrestin 2 recruitment may also be used for the treatment for alcohol use disorders and other co-occurring psychiatric disorders.

Those skilled in the art will recognize that numerous modifications can be made to the specific implementations described above. The implementations should not be limited to the particular limitations described. Other implementations may be possible.

We claim:

1. A compound selected from the group consisting of:

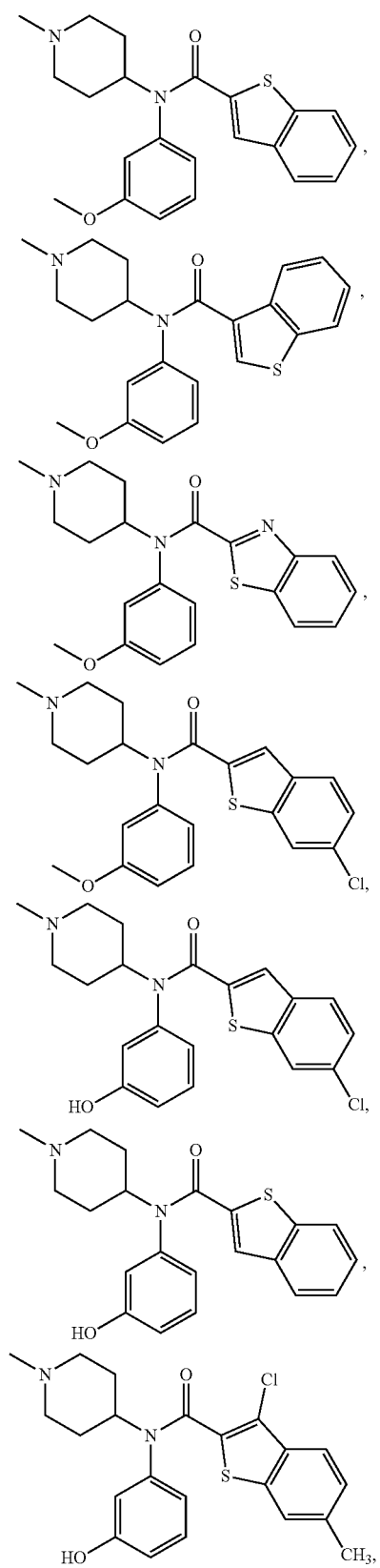

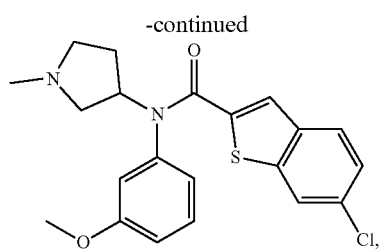

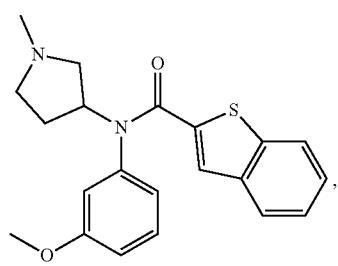

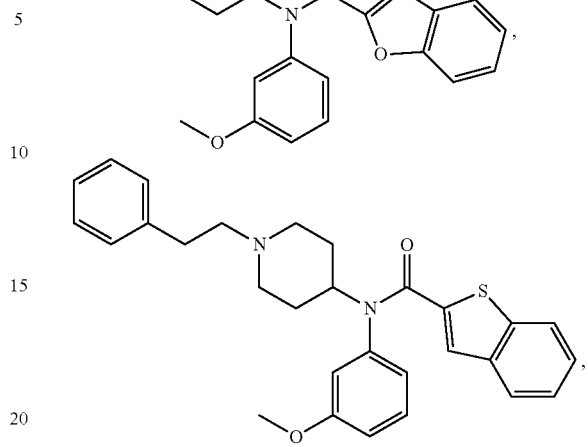

and a pharmaceutically acceptable salt or hydrate thereof.

2. A pharmaceutical composition comprising a compound of claim 1, or a pharmaceutically acceptable salt thereof.

3. A method of treating alcohol use disorders in a patient, wherein the method comprises administering to a patient in need thereof an effective amount of the pharmaceutical composition of claim 2.

* * * * *